(12) United States Patent
Tanassi et al.

(10) Patent No.: US 7,942,529 B2
(45) Date of Patent: May 17, 2011

(54) METHOD FOR THE OPTIMIZATION OF THE CONDITIONS OF EXECUTION OF THE VISION CONTRAST TEST, AND CORRESPONDING SYSTEM

(75) Inventors: Cesare Tanassi, Ponte Della Priula (IT); Gianluigi Meneghini, Selvazzano Dentro (IT); Walter Zanette, San Fior (IT)

(73) Assignee: SIFI Diagnostic SpA, Aci S. Antonio (IT)

( * ) Notice: Subject to any disclaimer, the term of this patent is extended or adjusted under 35 U.S.C. 154(b) by 0 days.

(21) Appl. No.: 12/532,623

(22) PCT Filed: Mar. 20, 2008

(86) PCT No.: PCT/EP2008/053373

§ 371 (c)(1),
(2), (4) Date: Sep. 22, 2009

(87) PCT Pub. No.: WO2008/113853

PCT Pub. Date: Sep. 25, 2008

(65) Prior Publication Data

US 2010/0103271 A1    Apr. 29, 2010

(30) Foreign Application Priority Data

Mar. 22, 2007    (IT) .............................. MI2007A0577

(51) Int. Cl.
*A61B 3/02*    (2006.01)

(52) U.S. Cl. .......................... 351/243; 351/210; 351/239
(58) Field of Classification Search ................... 351/243
See application file for complete search history.

(56) References Cited

U.S. PATENT DOCUMENTS

| 4,285,580 | A | 8/1981 | Murr |
| 5,066,117 | A | 11/1991 | Matsumura |
| 5,078,486 | A | 1/1992 | Evans |
| 5,568,209 | A | 10/1996 | Priester et al. |
| 6,715,878 | B1* | 4/2004 | Gobbi et al. .................. 351/243 |
| 2006/0007170 | A1* | 1/2006 | Wilson et al. ................. 345/173 |
| 2007/0171363 | A1* | 7/2007 | Chen et al. .................... 351/200 |
| 2007/0200927 | A1* | 8/2007 | Krenik ........................... 348/47 |

FOREIGN PATENT DOCUMENTS

WO    WO-2006/088383    8/2006

OTHER PUBLICATIONS

International Search Report and Written Opinion of the International Searching Authority for PCT/EP2008/053373, mailed on Aug. 19, 2008, 13 pages.

\* cited by examiner

*Primary Examiner* — Jessica T Stultz
(74) *Attorney, Agent, or Firm* — Levine Bagade Han LLP

(57) ABSTRACT

Described herein is a method for optimization of the conditions of execution of the vision contrast test and the corresponding system with which to implement said method so as to be able to guarantee optimal conditions throughout the test session even when not it is not possible to respect the standards. Furthermore, the method comprises a self-calibration procedure, which definitively eliminates the operations of calibration of the system by specialized centers.

7 Claims, 3 Drawing Sheets

METHOD FOR THE OPTIMIZATION OF THE CONDITIONS OF EXECUTION OF THE VISION CONTRAST TEST, AND CORRESPONDING SYSTEM

CROSS-REFERENCE TO RELATED APPLICATIONS

This application is a U.S. National Phase of International Application No. PCT/EP2008/053373 filed Mar. 20, 2008, which claims priority to Italian Patent Application MI2007A000577 filed Mar. 22, 2007, the disclosures of which are incorporated herein by reference in their entirety.

FIELD OF THE INVENTION

The present invention relates to a method for optimization of the conditions of execution of the vision contrast test and corresponding system.

PRIOR ART

During optical or oculistic examinations, in order to explore particular functions of the visual apparatus, amongst which visual acuity in situations of controlled contrast, it is necessary to subject the patient to visual stimuli with different and calibrated contrasts in binocular vision.

Current computerized systems normally use LCDs, which undergo calibration in the factory, possibly repeated periodically in the laboratory, to guarantee a yield of the basic brightness that is correct for use of particular levels of brightness in the contrast test.

One problem lies in the intrinsic inconstancy of the brightness of the display device (hereinafter simply referred to as "display"), which is typically obtained using LCD technology, and in particular of the corresponding backlighting system. Many of the tests must provide a certification of the results, which is markedly affected by the constancy and the verifiability of the calibration and by the use of the correct ambient illumination.

Another, even more important, problem lies in the impossibility of controlling illumination of the environment in which the test is conducted, with consequent influence on the results of the test, which is based upon the perception of the brightness (luminance) and of the contrasts of the display system.

In the use of conventional optotypes, a manual control of the ambient light is used, aimed at obtaining an illumination of the environment that is constant during the tests. Unfortunately, however, the intensity of the light emitted by the light sources is never regulated in an absolute sense in relation to the optimal level of illumination that the testing environment should have.

Consequently, also tests that are based upon the display of computerized optotypes, which use LCDs, are not reliable in so far as the illumination of the environment is not only not precise, but may also not be adjustable, or may even vary while the test is being carried out, for example, on account of changes in the conditions of shading, and moreover added to this is the inconstant calibration of the LCD.

SUMMARY OF THE INVENTION

Consequently, the purpose of the present invention is to overcome all the aforesaid drawbacks and to indicate a system for managing at the same time the conditions of illumination of the environment and of brightness of the display in addition to calibrating the emission thereof in terms of white and colour balancing. A further purpose of the present invention is to provide a method and a corresponding system definitively eliminating the need to subject the display systems to periodic calibration.

Yet a further purpose of the present invention is to provide a system integrating a standard low-cost computer equipped with a display device.

Consequently, a particular object of the present invention is a method for optimization of the conditions of execution of the vision contrast test.

BRIEF DESCRIPTION OF THE DRAWINGS

Further purposes and advantages of the present invention will emerge clearly from the ensuing detailed description of an example of embodiment thereof (and of its variants) and from the annexed plates of drawings, which are provided purely by way of explanatory non-limiting example and in which.

DETAILED DESCRIPTION OF THE INVENTION

Figure 1:
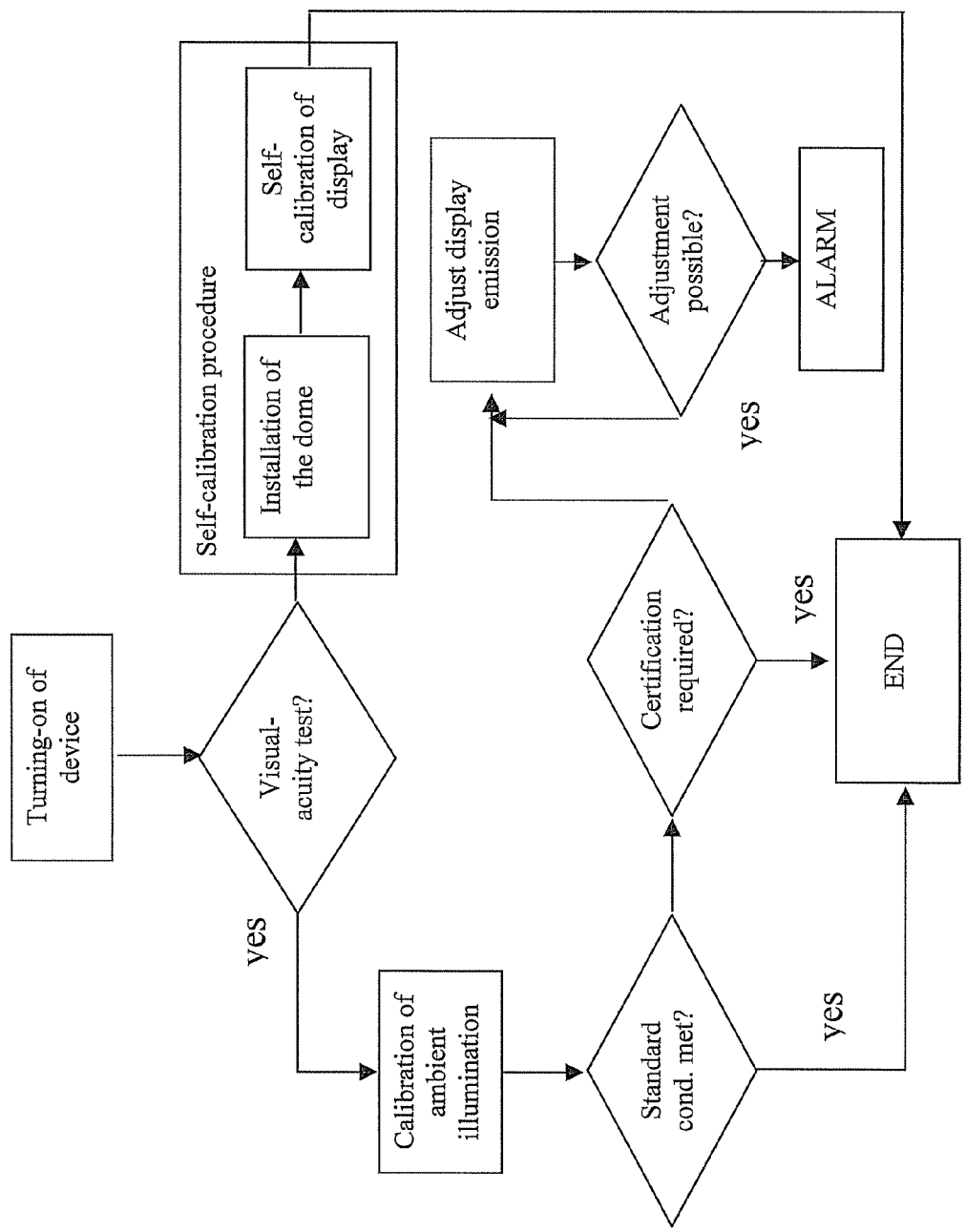
FIG. 1 is a flowchart representing the method.

The method forming the subject of the present invention comprises the steps described below in relation to precise conditions in accordance with the flowchart represented in FIG. 1.

Figure 2:
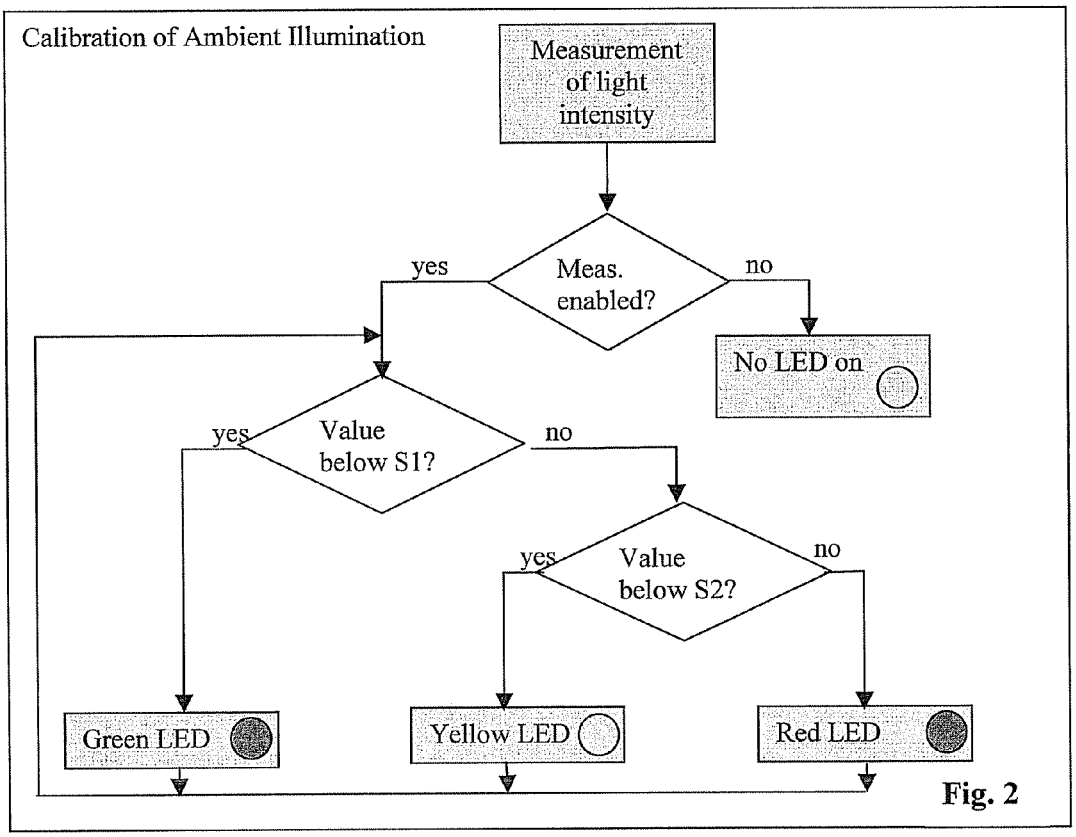
FIG. 2 illustrates the block "Calibration of Ambient Illumination" of the diagram of FIG. 1.

If a test on visual acuity is being carried out, the block "Calibration of Ambient Illumination" is executed, and, by means of a signalling device, the goodness of the conditions of ambient illumination is signalled, according to the flowchart represented in FIG. 2.

If the standard conditions have been met, it is possible to carry out the visual-acuity test (not appearing in the flowchart because it is in itself known).

If the conditions have not been met, the operator is asked whether he wishes to carry out a certified examination (i.e., an examination that respects a standard in itself known). If the answer is "YES", the procedure ends (END block) because it is not possible to proceed any further (for example, a red light lights up).

Otherwise, if it is not required to perform a certified examination, the "Adjust Display Emission" procedure is executed. Said procedure comprises the following steps:

a. if the conditions of ambient illumination are higher than the norm, then the brightness of the display is increased;

b. otherwise, if the conditions of ambient illumination are lower than the norm, then the brightness of the display is decreased;

c. if it is not possible to vary the brightness so as to obtain an effective test session, then the event is signalled, for example, with a red light, and the procedure starts again from step a in order to provide a real-time and efficient adjustment as any ambient condition varies;

d. if the adjustment has been successful, then the event is signalled, for example, with a green light.

Preferably, the Adjustment Display Emission procedure is executed in continuous mode, so as to provide a real time and efficient adjustment as any ambient condition varies.

The aforementioned procedure of "Calibration of Ambient Illumination" is executed according to the following steps:
a. the level of ambient illumination is measured;
b. if the value of illumination is within a threshold S1, then the event is signalled as positive and, for example, a green light lights up;
c. if the conditions are within a threshold S2, then the event is signalled as intermediate and, for example, a yellow light lights up;
d. if the conditions are not within the threshold S2, then the event is signalled as negative and, for example, a red light lights up.

Figure 3:
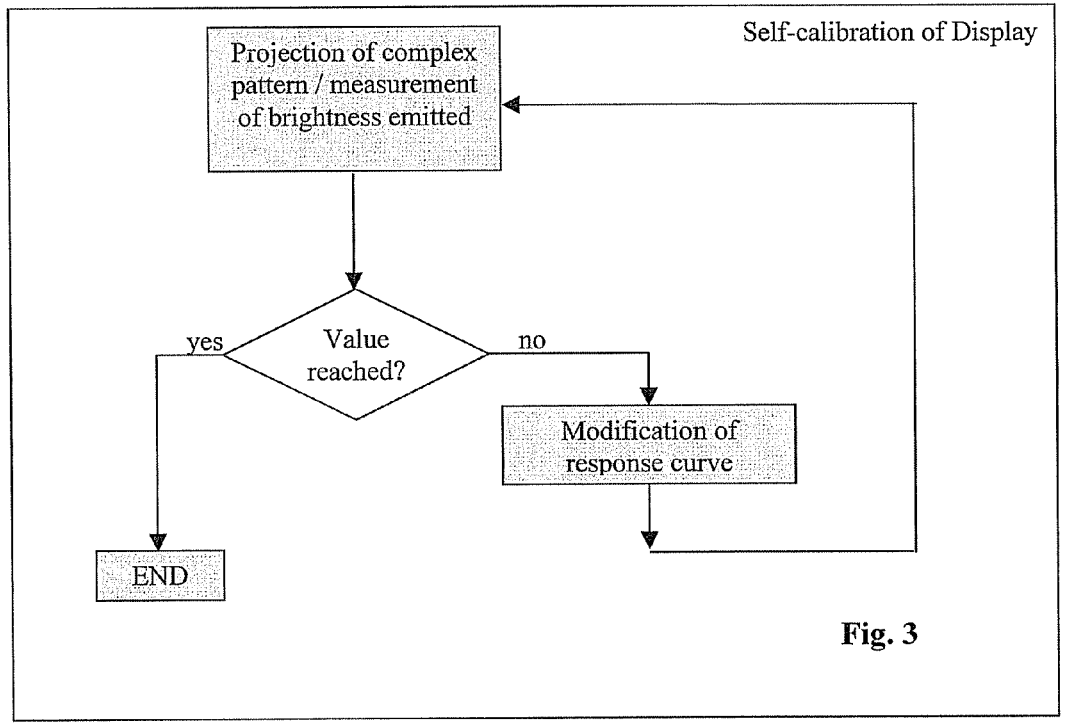
FIG. 3 illustrates the block "Self-calibration of Display" of the diagram of FIG. 1.

Preferably, the Calibration of Ambient Illumination procedure is executed in continuous mode, so as to provide a real time and efficient calibration as any ambient condition varies. If a visual-acuity test is not being carried out, but rather self-calibration of the display is required, then, once the reflecting dome has been mounted, operation of which will be illustrated hereinafter, the system executes, in a completely autonomous way, the self-calibration test in accordance with the flowchart represented in FIG. 3; hence the complete process is the following:
a. the reflecting dome is installed;
b. the colour-detection sensor is brought up to the display for white balancing;
c. a sequence of images is projected, and the brightness and colours emitted by the display are detected;
d. if necessary, the emission curve is corrected, and the procedure returns to step b;
e. if the correction is not necessary, the procedure ends.

It is consequently clear that with the method described above it is possible to regulate the conditions of ambient illumination and calibrate the display to obtain certified tests on visual acuity of the patient.

Furthermore, it is in any case possible to obtain efficient tests, even though they do not respect any standard, which are based upon the compensation of the level of emission of the display in relation to the ambient conditions.

Figure 4:
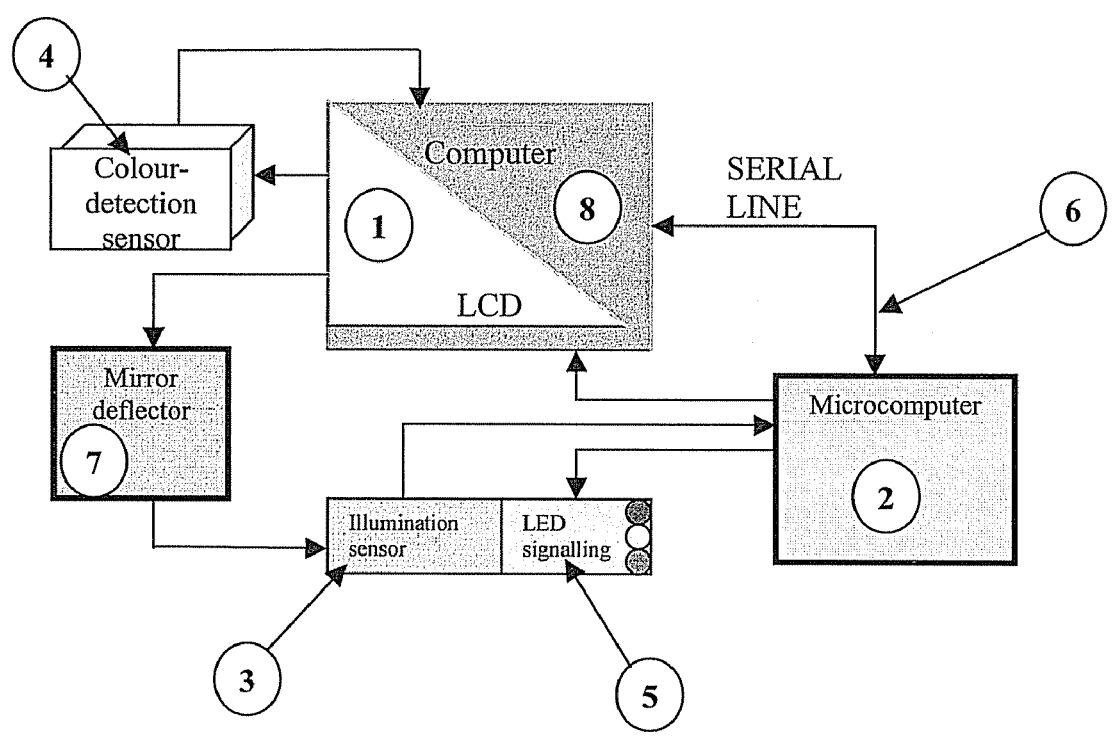
FIG. 4 represents the logic diagram of interconnection of the various devices making up the system.

A preferred embodiment of the system that enables implementation of said method comprises (FIG. 4):
a display 1, for example, an LCD;
a microcomputer 2, for example, integrated in the package of the display 1;
an illumination sensor 3, integrated in the frame of the display 1;
a colour-detection sensor 4, integrated in the frame of the display 1;
a signalling device 5 with coloured LEDs (or multitone audio);
an interface 6, for example, a USB interface, for connection between said microcomputer 2 and another computer;
a mirror dome or deflector 7; and
a standard computer 8.

The microcomputer 2 is connected to the sensors 3 and 4 and to the device 5 and has an interface 6.

The microcomputer 2 analyses the information obtained from the sensor 3 and enables lighting-up of the signalling device 5 in according to the procedure set forth above.

The microcomputer 2 is connected to the computer 8 by means of said interface 8 to enable modification of the control signals that the graphic card of the computer 8 emits in driving the display 1, when it is not possible to respect the standard ambient conditions. Consequently, it is clear that the display 1 is connected to the computer 8.

In the self-calibration step, it is necessary to convey the brightness emitted by the display onto the sensor 3, as likewise it is necessary to bring the sensor 4 up to the display to adjust white balancing so that the microcomputer can regulate, via the computer 8, the emission of the graphic card with which the latter is equipped. Advantageously, use of a dome or deflector 7 during self-calibration means that the sensor 4 is not impinged upon by environmental light, but only by the light emitted by the display.

Lastly, in a preferred embodiment, said illumination sensor 3 is a TSL257-E35 manufactured by Texas Instruments, the intrinsic characteristics of construction of which guarantee its reliability, but above all robustness of the system in regard to disturbance on the supply and/or deriving from the environmental climatic conditions, so that the factory calibration of the circuitry that drives said component guarantees perfect behaviour of the system throughout its service life, without calling for any further intervention. It is clear that the fact of entrusting calibration of the display 1 to a sensor 4 of extremely high precision as compared to the precision of the device 1 radically solves the problem of maintenance interventions.

During the calibration step, the software that manages the microcomputer drives the computer 8, by means of its own graphic card, to display particular sequences of images appropriately composed, for the purpose of a better correction of the emission curve of the display in terms of brightness, contrast, red, blue, and green balancing.

The present invention can advantageously be implemented via a computer program, which comprises code means for implementation of part or all the steps of the method, when the program is run on a computer. Consequently, it is understood that the scope of protection extends to said computer program and moreover to computer-readable means, which comprise a recorded message, said computer-readable means comprising program-code means for the implementation of one or more steps of the method, when said program is run on a computer.

Variant embodiments of the non-limiting example described are possible, without thereby departing from the scope of protection of the present invention, including all the equivalent embodiments that can be made by a person skilled in the art.

The invention claimed is:

1. A system for optimizing conditions of execution of a vision contrast test, comprising:
a display device (1);
a microcomputer (2);
an illumination sensor (3) which is positioned to receive light emitted by the display device upon the illumination sensor;
a colour-detection sensor (4);
a signaling device (5);
a connection interface (6);
a mirror dome or deflector (7) which is positioned to direct the light emitted by the display device upon the illumination sensor and the colour-detection sensor; and
a computer (8), equipped with a graphic card, where the computer is in communication with the illumination sensor and signaling device, and further where the microcomputer regulates the graphic card via the computer.

2. The system according to claim 1, characterized in that said microcomputer (2) is connected to said illumination sensor (3), to said colour-detection sensor (4), and to a connection interface (6).

3. The system according to claim 1, characterized in that the display device (1) is an LCD.

4. The system according to claim 1, characterized in that the signaling device (5) has coloured lights.

5. The system according to claim 1, characterized in that the signalling device (5) has a multitone buzzer.

6. The system according to claim 1, characterized in that the connection interface is of a USB or RS232 type.

7. The system according to claim 6, characterized in that any adjustment of the emission of the display (1) is driven by the microcomputer through the USB interface, via said computer (8), given that the graphic card of said computer (8) is connected to said display (1).

\* \* \* \* \*